United States Patent [19]

Roby et al.

[11] Patent Number: 5,618,313
[45] Date of Patent: Apr. 8, 1997

[54] ABSORBABLE POLYMER AND SURGICAL ARTICLES FABRICATED THEREFROM

[75] Inventors: Mark S. Roby, Killingworth; Donald S. Kaplan, Weston; Cheng-Kung Liu, Norwalk; Steven L. Bennett, Southington, all of Conn.

[73] Assignee: United States Surgical Corporation, Norwalk, Conn.

[21] Appl. No.: 320,814

[22] Filed: Oct. 11, 1994

[51] Int. Cl.$^6$ .................................... A61B 17/04
[52] U.S. Cl. .................. 606/230; 606/228; 606/229; 525/411; 525/415; 525/408; 528/354
[58] Field of Search .................... 606/228–231; 525/408, 415, 411; 528/354

[56] References Cited

U.S. PATENT DOCUMENTS

| | | |
|---|---|---|
| 2,668,162 | 2/1954 | Lowe . |
| 2,683,136 | 7/1954 | Higgins . |
| 2,703,316 | 3/1955 | Schneider . |
| 2,758,987 | 8/1956 | Salzberg . |
| 2,937,223 | 2/1976 | Roth . |
| 3,225,766 | 12/1965 | Baptist et al. . |
| 3,268,486 | 8/1966 | Klootwijk . |
| 3,268,487 | 8/1966 | Klootwijk . |
| 3,297,033 | 1/1967 | Schmitt et al. . |
| 3,422,181 | 1/1969 | Chirgwin, Jr. . |
| 3,442,871 | 5/1969 | Schmitt et al. . |
| 3,463,158 | 8/1969 | Schmitt et al. . |
| 3,468,853 | 9/1969 | Schmitt et al. . |
| 3,531,561 | 9/1970 | Trehu . |
| 3,565,869 | 2/1971 | DeProspero . |
| 3,597,449 | 8/1971 | DeProspero et al. . |
| 3,620,218 | 11/1971 | Schmitt et al. . |
| 3,626,948 | 12/1971 | Glick et al. . |
| 3,636,956 | 1/1972 | Schneider . |
| 3,733,919 | 5/1973 | Rupp, II . |
| 3,736,646 | 6/1973 | Schmitt et al. . |
| 3,739,773 | 6/1973 | Schmitt et al. . |
| 3,772,420 | 11/1973 | Glick et al. . |
| 3,781,349 | 12/1973 | Ramsey et al. . |
| 3,784,585 | 1/1974 | Schmitt et al. . |
| 3,792,010 | 2/1974 | Wasserman et al. . |
| 3,797,499 | 3/1974 | Schneider . |
| 3,839,297 | 10/1974 | Wasserman et al. . |
| 3,846,382 | 11/1974 | Ramsey et al. . |
| 3,867,190 | 2/1975 | Schmitt et al. . |
| 3,878,284 | 4/1975 | Schmitt et al. . |
| 3,896,802 | 7/1975 | Williams . |
| 3,902,497 | 9/1975 | Casey . |
| 3,982,543 | 9/1976 | Schmitt et al. . |
| 3,987,937 | 10/1976 | Coucher . |

(List continued on next page.)

FOREIGN PATENT DOCUMENTS

| | | |
|---|---|---|
| 0411545 | 2/1991 | European Pat. Off. . |
| 0440448 | 8/1991 | European Pat. Off. . |
| 779291 | 1/1955 | United Kingdom . |
| 1332505 | 10/1970 | United Kingdom . |
| 1414600 | 2/1974 | United Kingdom . |
| 2102827 | 7/1982 | United Kingdom . |

OTHER PUBLICATIONS

D. K. Gilding et al., "Biodegradable Polymers for Use in Surgery–Polyglycolic/Poly(Lactic Acid) Homo & Copolymers:1" Polymer vol. 20, pp. 1459–1464 (1979).

D.F. Williams (ed) Biocompatibility of Clinical Implant Materials, vol. II Chapter 9: "Biodegradable Polymers" (1981).

Medical & Biological Engineering & Computing Supplement, vol. 31, Jul. 1993, pp. S147–S151, C.X. Song et al., Biodegradable copolymers based on p–dioxanone for medical application.

Copy of Search Report.

*Primary Examiner*—Michael Powell Buiz
*Assistant Examiner*—Mark S. Leonardo

[57] ABSTRACT

Absorbable copolymers are fabricated from a predominant component of dioxanone randomly copolymerized with minor amounts of other bioabsorbable monomers. The copolymers are useful in forming surgical articles, including both monofilament and multifilament sutures.

11 Claims, 2 Drawing Sheets

U.S. PATENT DOCUMENTS

| | | |
|---|---|---|
| 4,033,938 | 7/1977 | Augurt et al. . |
| 4,045,418 | 8/1977 | Sinclair . |
| 4,052,988 | 10/1977 | Doddi et al. . |
| 4,057,537 | 11/1977 | Sinclair . |
| 4,060,089 | 11/1977 | Noiles . |
| 4,137,921 | 2/1979 | Okuzumi et al. . |
| 4,157,437 | 6/1979 | Okuzumi et al. . |
| 4,243,775 | 1/1981 | Rosensaft et al. .............. 525/415 |
| 4,246,904 | 1/1981 | Kaplan . |
| 4,273,920 | 6/1981 | Nevin ............................ 528/361 |
| 4,275,813 | 6/1981 | Noiles ........................... 206/339 |
| 4,279,249 | 7/1981 | Vert et al. . |
| 4,360,565 | 11/1981 | Rosensaft et al. .............. 606/231 |
| 4,643,191 | 8/1987 | Bezwada et al. ................ 606/231 |
| 4,744,365 | 5/1988 | Kaplan et al. .................. 606/231 |
| 5,225,520 | 6/1993 | Kennedy et al. ................ 528/354 |
| 5,314,989 | 5/1994 | Kennedy et al. ................ 528/354 |
| 5,403,347 | 4/1995 | Roby et al. ..................... 606/230 |

# 5,618,313

ABSORBABLE POLYMER AND SURGICAL ARTICLES FABRICATED THEREFROM

TECHNICAL FIELD

The present invention relates to bioabsorbable copolymers fabricated from the random copolymerization of lactide and dioxanone, and more particularly to surgical articles made totally or in part therefrom, including both monofilament and multifilament sutures.

BACKGROUND OF THE INVENTION

Polymers and copolymers of, and surgical devices made from lactide and/or glycolide and/or related compounds are well-know. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo-and copolymers: 1," *Polymer*, Volume 20, pages 1459–1464 (1979), and D. F. Williams (ed.) *Biocompatibility Of Clinical Implant Materials,* Volume II, chapter 9: "Biodegradable Polymers" (1981).

Surgical devices prepared from copolymers containing dioxanone and lactide are known in the art.

U.S. Pat. No. 4,052,988 describes random copolymers containing dioxanone and up to 50 percent by weight of other copolymerizable monomers which produce non-toxic and absorbable copolymers.

U.S. Pat. No. 4,643,191 describes copolymers of dioxanone and lactide fabricated by initially polymerizing dioxanone monomer to form a mixture of dioxanone homopolymer and dioxanone monomer, adding lactide monomer to the mixture, and subsequently polymerizing. The '191 patent does not describe copolymers fabricated by the random polymerization of lactide and dioxanone.

As described above, bioabsorbable sutures are known in the art. A desirable characteristic of a bioabsorbable suture is its ability to exhibit and maintain desired tensile properties for a predetermined time period followed by rapid absorption of the suture mass (hereinafter "mass loss".)

Absorbable multifilament sutures such as Dexon, Vicryl, and Polysorb commercially available from Davis & Geck (Danbury, Conn.), Ethicon, Inc. (Sommerville, N.J.), and United States Surgical Corporation (Norwalk, Conn.,) respectively, are known in the industry as short term absorbable sutures. The classification short term absorbable sutures generally refers to surgical sutures which retain about 20 percent of their original strength at three weeks after implantation, with the suture mass being essentially absorbed in the body within about 60 to 90 days post implantation.

Long term absorbable sutures are generally known to be sutures which retain about 20 percent of their original strength at six or more weeks after implantation, with the suture mass being essentially absorbed in the body Within about 180 days post implantation. For example, PDS II, a synthetic absorbable monofilament suture, commercially available from Ethicon, Inc. (Sommerville, N.J.), retains about 20 to about 30 percent of its original strength at six weeks after implantation. However, PDS II exhibits minimal mass loss until 90 days after implantation with the suture mass being essentially absorbed in the body about 180 days after implantation. Maxon, commercially available from Davis & Geck (Danbury, Conn.) is another absorbable synthetic monofilament generally fitting this absorption profile.

Therefore, it would be advantageous to provide a long term bioabsorbable synthetic monofilament surgical suture which exhibits and maintains tensile properties and handling characteristics comparable to PDS II, while having a shorter and thus improved mass loss profile.

SUMMARY OF THE INVENTION

It has now been found that absorbable surgical articles may be formed from the random copolymerization of dioxanone and a minor component of other bioabsorbable monomers. Suitable bioabsorbable monomers include lactide and dioxanone.

Preferably, copolymers useful in forming surgical articles in accordance with the present invention include copolymers comprising a predominant component of dioxanone. A "predominant component" is a component which is present in an amount greater than about 95 weight percent. A "minor component" is a component which is present in an amount up to about 5 weight percent.

In a particularly useful embodiment the copolymers may be spun into fibers. The fibers can be fabricated into both monofilament and braided multifilament sutures. Preferably copolymers useful in this embodiment comprise at least about 4 percent lactide, the remainder being dioxanone.

Further provided is a process for manufacturing a suture exhibiting excellent energy and/or increased knot performance for a given size comprising the operations of extruding the block copolymer of the present invention at an extrusion temperature of from about 95° C. to about 180° C. to provide a monofilament fiber, stretching the solidified monofilament at a temperature of from about 30° C. to about 60° C. in water (or other suitable liquid medium) or at from about 25° C. to about 95° C. in air (or other suitable gaseous medium) at a stretch ratio of from about 3:1 to about 10:1 to provide a stretched monofilament. The stretched monofilament preferably is then frozen at a temperature of from about −25° C. to about 0° C. The suture then may be annealed with or without relaxation at a temperature of from about 40° C. to about 95° C. to provide the finished suture.

DESCRIPTION OF THE PREFERRED EMBODIMENTS

It has been found that monomers of lactide and dioxanone (with dioxanone as the predominant component thereof) can advantageously be randomly copolymerized to form a copolymer useful in forming surgical sutures.

Such random copolymers include copolymers in which dioxanone comprises at least 95 weight percent of the copolymer. Preferably, dioxanone comprises about 96–97 weight percent of the copolymer. The dioxanone may be copolymerized with any absorbable monomer, with lactide being preferred. These copolymers can be synthesized by known methods. See, for example, U.S. Pat. Nos. 4,653,497; 4,838,267; 4,605,730; 4,788,979, and U.S. patent application Ser. No. 08/036,922 the disclosures of which are incorporated herein by reference. Such copolymers of dioxanone have a molecular weight such that they exhibit an inherent viscosity of from about 1.2 to about 3 dl/g measured at 30° C. and a concentration of 0.25 g/dl in hexafluoroisopranol (HFIP).

Although it is preferred to fabricate surgical sutures from the disclosed copolymers, a wide variety of surgical articles can be manufactured from the copolymer of the present invention. These include but are not limited to clips and other fasteners, staples, sutures, pins, screws, prosthetic devices, wound dressings, drug delivery devices, anastomosis rings, and other implantable devices. Fibers made from the copolymers of this invention can be knitted or woven with other fibers, either absorbable or nonabsorbable to form meshes or fabrics. The compositions of this invention can also be used as an absorbable coating for surgical devices. Surgical articles can be formed from the copolymers using any know technique, such as, for example, extrusion, molding and/or solvent casting. The copolymers can be used alone, blended with other absorbable compositions, or in combination with non-absorbable components.

Multifilament sutures of the present invention may be made by methods known in the art. Braid constructions such as those disclosed and claimed in U.S. Pat. Nos. 5,059,213 and 5,019,093 are suitable for multifilament sutures herein.

A suitable process for the manufacture of monofilament sutures comprises the operations of melt extruding the resin at an extrusion temperature of from about 95° C. to about 180° C. to provide a monofilament, stretching the solidified monofilament at a temperature of from about 30° C. to about 60° C. in water (or other suitable liquid medium) or at from about 25° C. to about 95° C. in air (or other suitable gaseous medium) at a stretch ratio of from about 3:1 to about 10:1 to provide a stretched monofilament. Optionally, the stretched monofilament may be stretched again in air or other suitable gaseous medium preferably at 60° C. to about 95° C. Preferably, the monofilament is then frozen at a temperature of from about −25° C. to about 0° C. The suture may then be annealed at a temperature of from about 40° C. to about 95° C. to provide the finished suture.

Figure 1A:
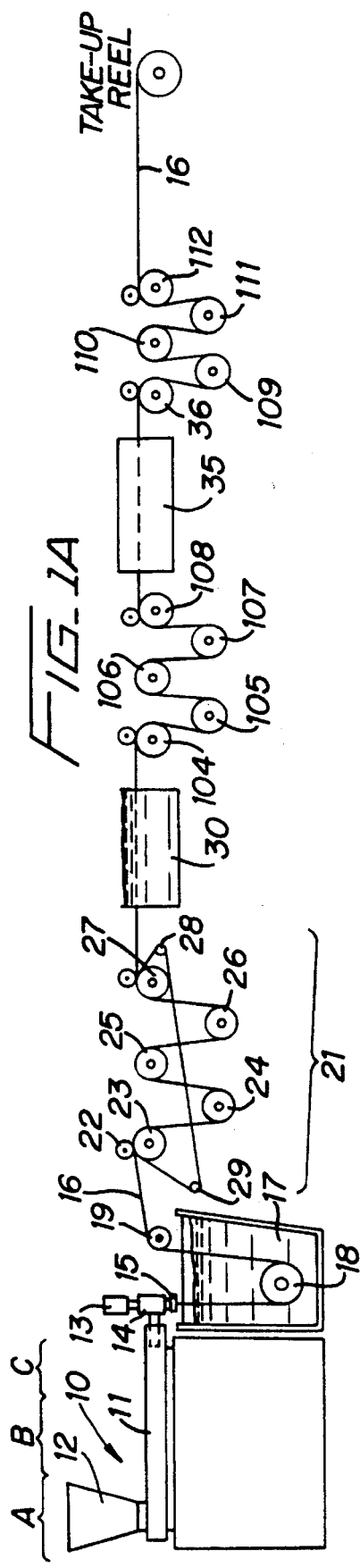
FIG. 1A is a schematic illustration of an apparatus which is suitable for manufacturing the monofilament suture of this invention; and, FIG. 1B is a modification of the apparatus of FIG. 1A which is particularly suitable for manufacturing the monofilament sutures of the present invention of smaller size, e.g., sizes 3/0 and smaller.

FIG. 1A schematically illustrates a monofilament suture manufacturing operation which is especially suitable for producing larger size sutures, e.g., those of sizes 2/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the block copolymers of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 10 cm. If desired, a chimney (not shown), or shield, can be provided to isolate monofilament 16 from contact with air currents which might otherwise affect the cooling of the monofilament in an unpredictable manner. In general, barrel zone A of the extruder can be maintained at a temperature of from about 80° C. to 105° C., zone B at from about 100° C. to 180° C. and zone C at from about 120° C. to about 180° C. Additional temperature parameters include: metering pump block 13 at from about 120° C. to about 180° C., spin pack 14 at from about 120° C. to about 180° C., spinneret 15 at from about 120° C. to about 180° C. and quench bath at from about 15° C. to about 50° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament enters first godet station 21.

First godet station 21 is equipped with five individual godets around which monofilament 16 is wrapped. First godet 23 is provided with nip roll 22 to prevent slippage which might otherwise result. Upon entering first godet station 21, monofilament 16 passes over first godet 23, under second godet 24, over third godet 25, under fourth godet 26 and over fifth godet 27. Fifth godet 27 is proximally located to separation roller 28 which is provided with a plurality of laterally spaced circumferential grooves which act as guides for monofilament 16. After monofilament 16 passes over fifth godet 27 it wraps around a groove on separation roller 29 located proximal to first godet station 23. Monofilament 16 wraps around separation roller 29, ascends up to first godet 23 and continues onward to the remaining godets in the manner just described. When the monofilament passes over the fifth godet 27 a second time, it may be wrapped around a second groove on separation roller 28. The monofilament then extends back to separation roller 29 and around a corresponding groove thereon. The monofilament may pass through first godet station 21 any desired number of times. The solidified monofilament is thus allowed to dwell at ambient conditions before the monofilament enters heating unit 30. In this fashion monofilament 16 is aged or exposed to ambient conditions for a desired period of time prior to being stretched.

It is to be understood that aging or exposing the monofilament to ambient conditions for a predetermined period of time prior to drawing the monofilament can be accomplished in many different ways. For example, any number of godets may be employed to provide the dwell period. In addition, the arrangement of the godets can be varied. Also, other structures suitable for providing aging of the monofilament prior to stretching will be apparent to those skilled in the art.

Monofilament 16 passing from godet 27 is stretched, e.g., with stretch ratios on the order of from about 2:1 to about 7:1 and preferably from about 3:1 to about 5:1, to effect its orientation and thereby increase its tensile strength.

In the stretching operation shown in FIG. 1A, generally suitable for larger size sutures, e.g., sizes 2 to 2/0, monofilament 16 is drawn through hot water (or other suitable liquid medium) draw bath 30 by means of godets 104, 105, 106, 107 and 108 or any other suitable arrangement of godets which rotate at a higher speed than godet station 21 to provide the desired stretch ratio. The temperature of hot water draw bath 30 is advantageously from about 30° C. to about 60° C. and preferably is from about 40° C. to about 50° C.

Figure 1B:
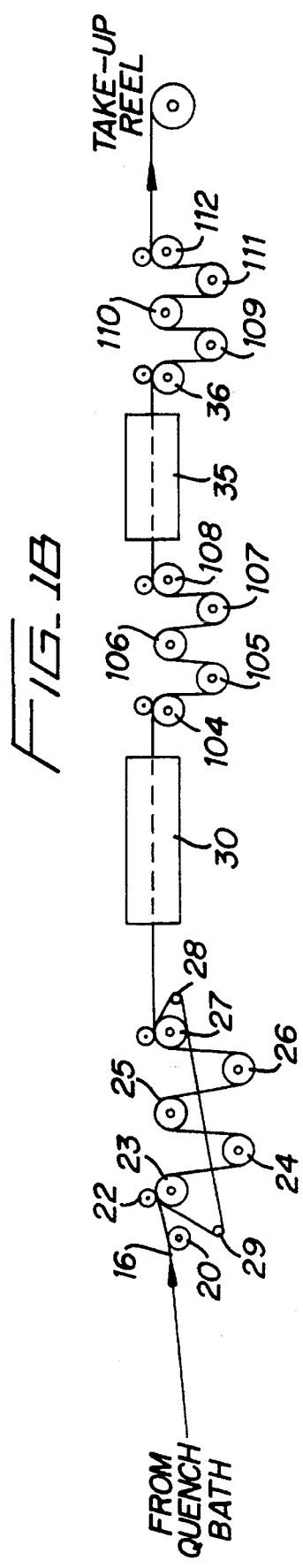

In an alternative stretching operation shown in FIG. 1B, generally preferred for smaller sutures sizes, e.g., sizes 3/0 to 8/0, monofilament 16 is drawn by godets 104, 105, 106, 107, and 108 or any other suitable godet arrangement through hot air convection oven chamber 30' at a temperature of from about 25° C. to about 95° C. and preferably from about 40° C. to about 80° C. to provide the desired amount of stretch.

Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 36, 109, 110, 111, and 112 or any other suitable godet arrangement through second hot air oven chamber 35 at a temperature of from about 40° C. to about 95° C. and preferably from about 50° C. to about 90° C. During the relaxation process, at these temperatures, monofilament 16 will generally recover to within about 80 to about 98 percent, and preferably to within about 90 percent, of its pre-annealed length to provide the finished suture. For relaxation, the third godet station rotates at a slower speed than the second godet station, thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 40° C. to about 95° C., as described in U.S. Pat. No. 3,630,205. After a suitable, period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

Figure 2:
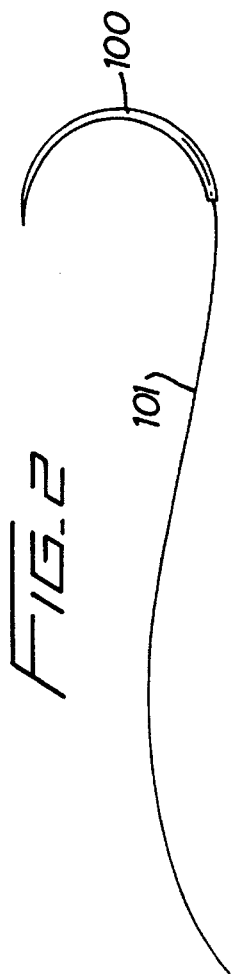
FIG. 2 is a perspective view of a suture of the present invention attached to a needle.

The suture of the present invention, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present invention in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

In order that those skilled in the art may be better able to practice the present invention, the following examples are given as an illustration of the preparation of copolymers described herein as well as of the preparation and superior characteristics of the sutures described herein. It should be noted that the invention is not limited to the specific details embodied in the examples.

EXAMPLE 1

L-lactide (180 grams) and 1,4 dioxane-2-one (5184 grams) were added to a reactor along with 1 gram of stannous octoate. The mixture was heated and placed at 100° C., with stirring under a nitrogen atmosphere for 24 hours. The L-lactide/1,4 dioxane-2-one copolymer was then sampled.

The reaction product was isolated, comminuted, and treated to remove residual reactants using known techniques. The copolymer was then heated under vacuum to remove residual water, residual solvent, and/or unreacted monomer.

COMPARATIVE EXAMPLE 1

1,4 dioxane-2-one (5000 grams) were added to a reactor along with 1 gram of stannous octoate. The mixture was heated and placed at 100° C., with stirring under a nitrogen atmosphere for 24 hours. The 1,4 dioxane-2-one homopolymer was then sampled.

The reaction product was isolated, comminuted, and treated to remove residual reactants using known techniques. The homocopolymer was then heated under vacuum to remove residual water, residual solvent, and/or unreacted monomer.

COMPARATIVE EXAMPLE 2

1,4 dioxane-2-one (4400 grams) and L-lactide (275 grams) were added to a reactor along with 1 gram of stannous octoate. The mixture was heated and polymerized at 100° C. for 24 hours. The L-lactide/1,4 dioxane-2-one polymer was then sampled.

Table I below sets forth typical conditions for extruding, stretching various sizes of sutures in accordance with this invention. All of the monofilament sutures were fabricated from the resin of Example 1 and Comparative Examples 1 and 2.

TABLE I

CONDITIONS OF MANUFACTURING OF MONOFILAMENTS

| | Example 1 | Comparative Example 1 | Comparative Example 2 |
|---|---|---|---|
| Suture Size | 3/0 | 3/0 | 3/0 |
| Process Conditions | | Extrusion Operation | |
| extruder screw, rpm | 1.1 | 1.6 | 1.5 |
| pump rpm | 5.3 | 10.3 | 10.6 |
| barrel temp., °C., zone A | 100 | 100 | 100 |
| barrel temp., °C., zone B | 165 | 130 | 120 |
| barrel temp., °C., zone C | 165 | 132 | 125 |
| clamp temp., °C., | 170 | 134 | 128 |
| adapter temp., °C. | 160 | 135 | 120 |
| pump temp., °C. | 170 | 135 | 121 |
| spinneret temp., °C. | 160 | 140 | 120 |
| barrel melt temp., °C. | 161 | 127 | 125 |
| pump melt temp., °C. | 162 | 133 | 118 |
| spinneret melt temp., °C. | — | 133 | 119 |
| barrel pressure, psi | 1100 | 2000 | 1300 |
| pump pressure, psi | 500 | 500 | 500 |
| spinneret pressure, psi | 2140 | 2620 | 3050 |
| pump size, cc per revolution | 0.297 | 0.16 | 0.16 |
| diameter of spinneret orifices, mm | 1.25 | 1.25 | 1.25 |
| no. of spinneret orifices | 1 | 1 | 1 |
| quench bath temp., °C. | 40 | 18 | 33 |

| | Example 1 | Comparative Example 1 | Comparative Example 2* |
|---|---|---|---|
| Process Conditions | | Stretching (Orienting) Operation | |
| oven temp., °C. | — | — | 70 |
| first godet, mpm | 4 | 4 | 3 |
| second godet, mpm | 16.6 | 20 | 14.1 |
| second oven temp., °C. | 90 | 100 | 63 |
| third godet, mpm | 24 | 26 | 18.4 |
| draw ratio | 6:1 | 6.5:1 | 6.1:1 |

*Comparative Example 2 was stored in a freezer at −15° C. for 18 hours before the stretching operation

| | Example 1 | Comparative Example 1 | Comparative Example 2 |
|---|---|---|---|
| Process Conditions | | Annealing Operation | |
| oven temp., °C. | 85 | 85 | 85 |
| time (hrs.) | 18 | 18 | 6 |
| relaxation (%) | 5 | 5 | 5 |

The physical properties of the sutures and the procedures employed for their measurement are set forth in Table II as follows:

TABLE II

PROCEDURES FOR MEASURING PHYSICAL PROPERTIES OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm$^2$ | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |

Measurements of knot pull, percent elongation, tensile strength and strain energy were carried out employing an Instron Corporation (Canton, Mass.) Tensile Tester, model no. 1122, equipped with yarn grips and operated with a gauge length of 127 mm and a crosshead speed of 51 mm/min. The physical properties of the monofilament sutures produced in accordance with the conditions of Table I were measured at 21° C. and 50 percent humidity.

Table III below sets forth a side by side comparison of the physical properties of the sutures of Example 1, Comparative Example 1, Comparative Example 2, and PDSII. PDSII, commercially available from Ethicon, Inc., Sommerville N.J., is made from a homopolymer of polydioxanone.

TABLE III

| Physical Property | Example 1 | Comparative Example 1 | Comparative Example 2 | PDS II |
|---|---|---|---|---|
| diameter (mm) | 0.293 | 0.292 | 0.312 | 0.308 |
| knot-pull strength (kg) | 2.2 | 2.8 | 1.9 | 2.5 |
| Young's Modulus (kpsi) | 142 | 224 | 130 | 210 |
| Straight-pull strength (kg) | 3.4 | 4.4 | 2.9 | 3.9 |
| Strain energy 0–5% (kg-mm) | 1.61 | 2.13 | 1.01 | 1.83 |
| Strain energy 0–10% (kg-mm) | 5.96 | 8.64 | 4.08 | 6.52 |
| Elongation (%) | 40 | 33 | 45 | 45 |
| Tensile strength (kg/mm$^2$) | 50 | 66 | 38 | 53 |

As the data in Tables III illustrates, the suture made of the copolymers provided herein shows physical properties comparable to PDSII. The data in Table III further shows that sutures of Comparative Example II, i.e. sutures prepared from random copolymers containing about 94 percent dioxanone and about 6 percent lactide have inferior characteristics in at least straight-pull and tensile strength properties when compared to sutures fabricated from the copolymers provided herein.

EXAMPLE 3

IN VITRO STRENGTH RETENTION

Figure 3A:
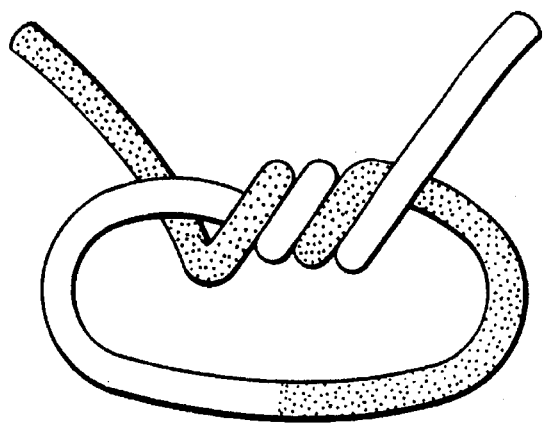
FIG. 3A–3C illustrate the formation of the knot which was employed in the loop-pull test used in Example 3.
Figure 3B:
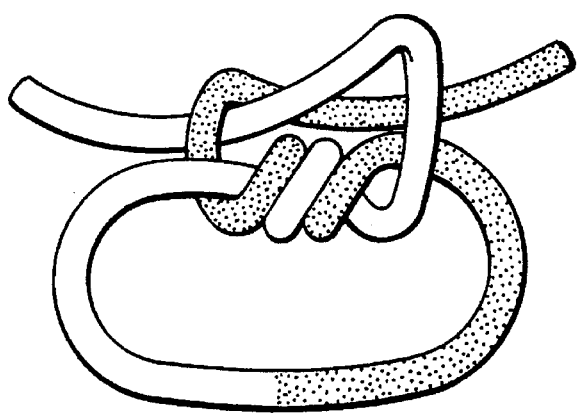
Figure 3C:
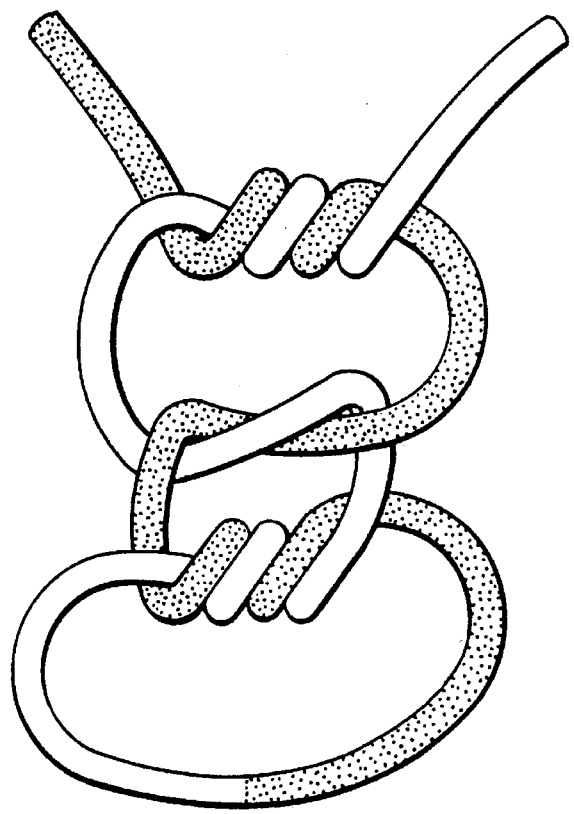

Monofilament sutures manufactured in accordance with the above described process using the copolymer of Example 1 were tested for in vitro strength retention. In vitro loop-pull strength retention is indicative of in vivo strength retention. The in vitro strength retention of the suture was tested as follows:

To simulate in vivo conditions, the suture samples were stored in a container filled with Sorenson's buffer solution at 37° C. After various periods of time, the suture samples were then removed from the container to test their loop-pull strength. as follows. A knotted loop was formed in a test suture in three steps as shown in FIGS. 3A–3C. As shown in step 1 of FIG. 3A, each suture was given a double throw (left over right) around a 2 cm diameter cylinder. In Step 2, the free ends of the suture were set in a single throw (right over left) onto the initial throw of step 1. Finally, in step 3, another double throw (left over right) was set onto the single throw of Step 2 to complete the knot. The free ends of the suture were cut to approximately 0.5 inches and the loop was carefully eased from the cylinder.

Testing of the loop was carried out using an Instron Corporation (Canton, Mass.) Tensile Tester Model No. 4301, operated with a crosshead speed of 25 mm/min and equipped with flat grips, each having a pin over which the loop is positioned.

The results of the tests are presented in Table V hereinbelow. In the strength retention data reported in Table V, $T_n$ represents the time elapsed in weeks since the sample was placed in the solution, with n representing the number of weeks. For comparison purposes, the same tests were conducted on a Maxon suture, which is made from a glycolide/ glycolide-trimethylene carbonate/glycolide copolymer (commercially available in 1993 from Davis and Geck, Danbury, Conn.); PDSII suture, as mentioned above, which is made from polydioxanone homopolymer (commercially available from Ethicon, Inc., Summerville, N.J.); and Comparative Examples 1 and 2. All comparative tests were performed on size 3/0 sutures.

TABLE IV

| COMPOSITION | PERCENTAGE OF IN VITRO STRENGTH RETAINED | | | | | | | |
|---|---|---|---|---|---|---|---|---|
| | $T_1$ | $T_2$ | $T_3$ | $T_4$ | $T_6$ | $T_8$ | $T_{10}$ | $T_{12}$ |
| Maxon | 88 | 81 | 70 | 69 | 33 | — | — | — |
| PDSII | — | — | — | 84 | — | 34 | — | 10 |
| EXAMPLE I | — | 83 | — | 36 | 22 | 6 | — | — |
| COMPARATIVE EXAMPLE 1 | — | 64 | — | 41 | 28 | 7 | — | — |
| COMPARATIVE EXAMPLE 2 | — | 84 | — | 34 | 9 | — | — | — |

As the data in Table IV demonstrates, the suture of Example 1 exhibits in vitro strength retention comparable to Comparative Example 1 and Maxon.

EXAMPLE 4

IN VIVO MASS LOSS

It is well known in the art that the in vivo absorption profile (mass loss) is a profile of a section of a fiber after implantation in a suitable test animal, e.g, a rat, taken over a period of time of the amount of degradation. Those of skill in the art will further appreciate that this absorption is measured by calculating the median percent of the original cross-sectional area of the fiber section remaining after an intramuscular implantation for a predetermined number of days.

Monofilament sutures manufactured in accordance with Example 1 were tested for in vivo mass loss. To determine mass loss, six loops of size 3/0 suture were placed in the abdominal wall of 24 anesthetized female Sprague-Dawley rats weighing approximately 225–250 grams. Three loops of suture were symmetrically placed on each side of the abdominal wall midline. The entry of each suture loop was 10 mm from the midline. The suture passed into the peritoneum and exited 7 mm lateral from its entry sight. Thus, the plane of the suture loop was perpendicular to the midline. Each suture loop was separated from its neighbor by 2 cm. The suture was formed into a secure loop with a surgeons knot tied square with one additional throw (2=1= 1). The knot ears were cut to be 3 mm long.

Following placement of the suture loops, the skin was closed and secured with microporous wound closure tapes. Additional tape to skin adherence was achieved by using tincture of benzoin on the skin at a distance of 3 mm from the wound edges. The incision was dressed with sterile gauze pad and the animal bandaged circumferentially with 3" wide porous cloth tape. The animals were closely monitored until they were active and thereafter on a daily basis. Bandages and dressings were removed seven days after surgery. Each rat received two loops of Example 1 suture, Comparative Example 1 suture, and PDS II; one loop on each side of the midline, respectively.

Three animals were evaluated one week and 3, 4, 5, 6, and 8 months after implantation and the suture loops in tissue were retrieved. Blocks of embedded tissue were sectioned on a Reichert Jung 2065 microtome (Leica) using glass knives. Thick sections of tissue were removed until suture deep within the muscle was exposed. Four 2.5 micron sections were then cut at two levels, $\frac{1}{3}$ and $\frac{2}{3}$ through the blocks, and were mounted on two separate microscope slides.

A calibrated ocular micrometer was used to measure suture diameter. The proportion of suture absorbed was calculated, as a percent, by comparison to that same suture as it appeared at one week.

TABLE V

| | PERCENTAGE OF 3/0 SUTURE ABSORBED IN VIVO OVER TIME | | | | |
|---|---|---|---|---|---|
| | 3 Mo. | 4 mo. | 5 mo. | 6 mo. | 8 mo. |
| Example 1 | 41 | 60 | 90 | 96 | 100 |
| Comparative Example 1 | 24 | 44 | 62 | 76 | 100 |
| PSD II | 23 | 16 | 33 | 54 | 97 |

As can be seen from Table V, the suture of Example 1 was absorbed most rapidly, from about 41% at 3 months to about 100% at 8 months. The suture of Comparative Example 1 was absorbed more slowly, from about 24% at 3 months to about 100% at 8 months. The Ethicon PDSII was absorbed even more slowly, from 23% at 3 months to 97% at 8 months.

It will be understood that various methods may be made to the embodiments disclosed herein. Therefore, the above description should not be construed as limiting, but merely as exemplifications of preferred embodiments. Those skilled in the art will envision other modifications within the scope and spirit of the claim appended hereto.

What is claimed is:

1. A needle-suture combination, the suture comprising fibers spun from composition containing a copolymer, the copolymer consisting essentially of at least about 95 percent by weight dioxanone randomly combined with up to about 5 weight percent lactide.

2. The device of claim 1 wherein the random copolymer contains 3 to about 4 weight percent lactide. The device of claim 1 wherein the random copolymer possesses an inherent viscosity of about 1.2 to about 3.0 dl/g at 30° C. and a concentration of 0.25 g/dl in HFIP.

3. The medical device of claim 1 wherein said suture is a monofilament suture.

4. A size 3/0 suture fabricated from a random copolymer containing at least about 95 percent by weight dioxanone and up to about 5 weight percent lactide exhibiting upon implantation a mass loss of about 60% after 4 months.

5. The suture of claim 4 exhibiting a mass loss of about 90% after 4 months.

6. The suture of claim 4 exhibiting a mass loss of about 96% after 6 months.

7. The device of claim 1 comprising a medico-surgically useful substance.

8. A size 3/0 suture fabricated from a random copolymer of at least about 95 percent by weight dioxanone and up to about 5% by weight lactide exhibiting the following properties:

Energy 0–5% (kg-mm) 1 to about 2.5;

Energy 0–10% (kg-mm) 4 to about 9;

Knot pull (kg) about 1.8 to about 2.8;

Straight pull (kg) about 3 to about 4.5;

Tensile strength (kg/mm$^2$) 35 to 60.

9. A medical device comprising a random copolymer containing at least 95 percent by weight dioxanone and up to about 5 weight percent lactide and exhibiting upon implantation a mass loss of about 60% after 4 months.

10. The medical device of claim 9 exhibiting a mass loss of about 90% after 5 months.

11. The medical device of claim 9 wherein said medical device is selected from the group consisting of clips, staples, pins, screws, prosthetic devices, anastomosis rings, and growth matrices.

* * * * *